US00PP24492P2

(12) United States Plant Patent
Sorensen

(10) Patent No.: US PP24,492 P2
(45) Date of Patent: May 27, 2014

(54) ***CLEMATIS* PLANT NAMED 'YAKU050'**

(50) Latin Name: ***Clematis* hybrid**
Varietal Denomination: YAKU050

(76) Inventor: Peer Sorensen, Waitara (NZ)

( * ) Notice: Subject to any disclaimer, the term of this patent is extended or adjusted under 35 U.S.C. 154(b) by 141 days.

(21) Appl. No.: 13/385,655

(22) Filed: Feb. 28, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — June Hwu
(74) *Attorney, Agent, or Firm* — Cassandra Brigh

(57) ABSTRACT

A new and distinct *Clematis* hybrid named 'YAKU050' is disclosed, characterized by a single, rounded flowers with light pink tepals having a raspberry pink center bar. The new cultivar is a *Clematis* typically suited for ornamental container and landscape use.

2 Drawing Sheets

Latin name of the genus and species: *Clematis* hybrid.
Variety denomination: 'YAKU050'.

BACKGROUND OF THE INVENTION

The new cultivar is the result of a breeding program, resulting from a crossing made in 1996. The inventor is Peer Sorensen, a citizen of Denmark. The new variety was discovered as a seedling resulting from the crossing of the seed parent, *Clematis* hybrid 'Maria Boisselo', unpatented with the pollen parent *Clematis* hybrid 'Nelly Moser', unpatented. The discovery was made in 2000. Crossing and discovery was made at a commercial nursery in New Zealand.

After selecting and isolating the new cultivar, asexual reproduction of the new cultivar 'YAKU050' was first performed in a commercial nursery Waitara, in New Zealand, by vegetative cuttings in the Fall of 2000. The inventor maintained the original plant, and observed the clones for several years, to establish stability of the characteristics. 'YAKU050' has since produced multiple generations and has shown that the unique features of this cultivar are stable and reproduced true to type.

SUMMARY OF THE INVENTION

The cultivar 'YAKU050' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'YAKU050.' These characteristics in combination distinguish 'YAKU050' as a new and distinct *Clematis* cultivar:

1. Single, rounded flowers
2. Tepals with a raspberry pink bar in center.
3. 6 to 8 tepals per flower.

PARENTAL COMPARISON

Plants of the new cultivar 'YAKU050' are similar to the seed parent variety in most horticultural characteristics. However, 'YAKU050' differs in having different colored tepals than the seed parent variety.

Plants of the new cultivar 'YAKU050' are similar to the pollen parent variety in most horticultural characteristics. However, 'YAKU050' differs in having different shaped tepals than the pollen parent variety.

COMMERCIAL COMPARISON

Plants of the new cultivar 'YAKU050' are most similar to the commercial variety *Clematis* hybrid 'Bee's Jubilee' unpatented. Both *Clematis* varieties have similar plant habits, and produce similar amounts of tepals. 'YAKU050' differs from 'Bee's Jubilee' in having a lighter flower color. Additionally, plants of 'YAKU050' produce tepals of a different shape than those on plants of 'Bee's Jubilee'.

BRIEF DESCRIPTION OF THE PHOTOGRAPHS

Figure 1:
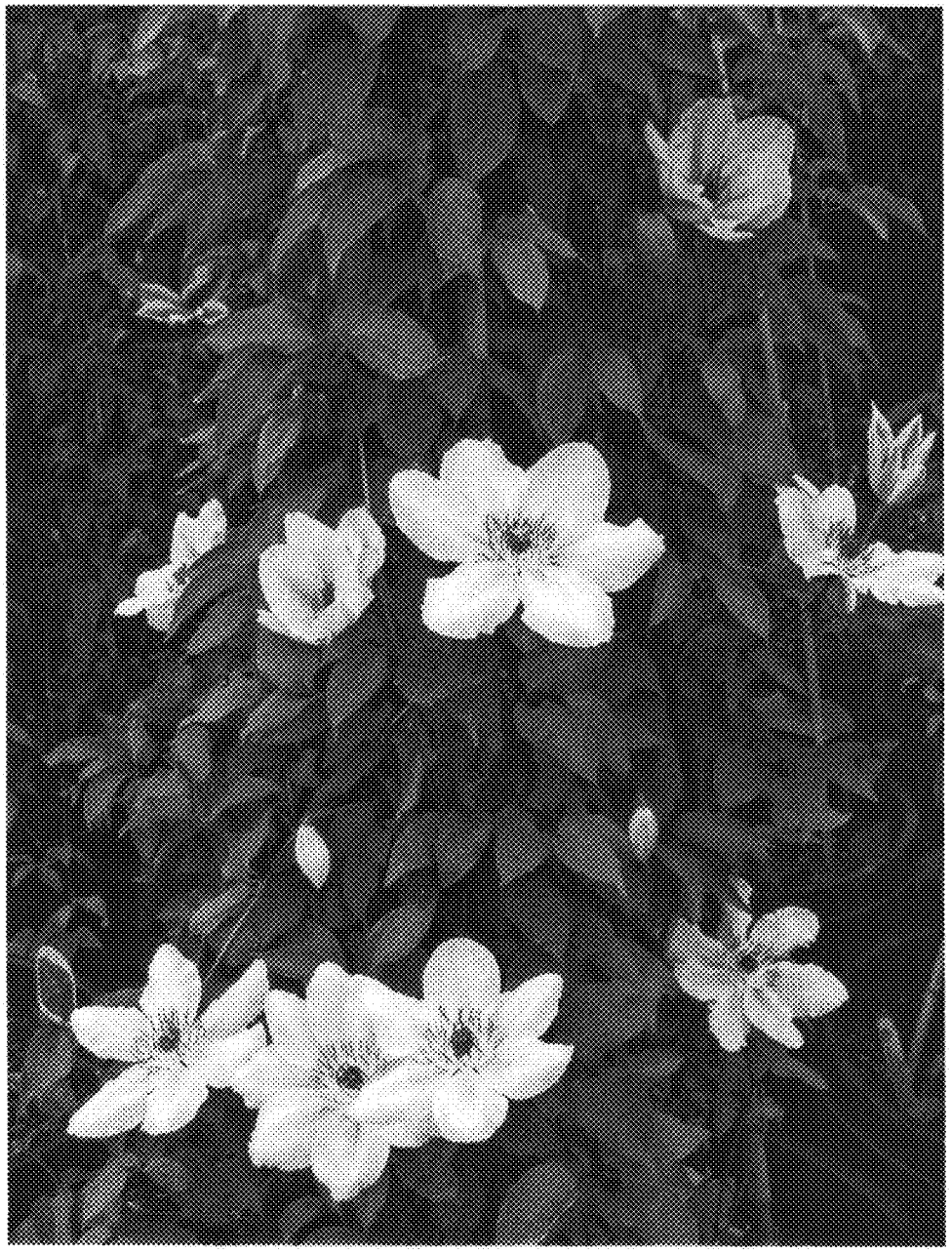
Figure 2:
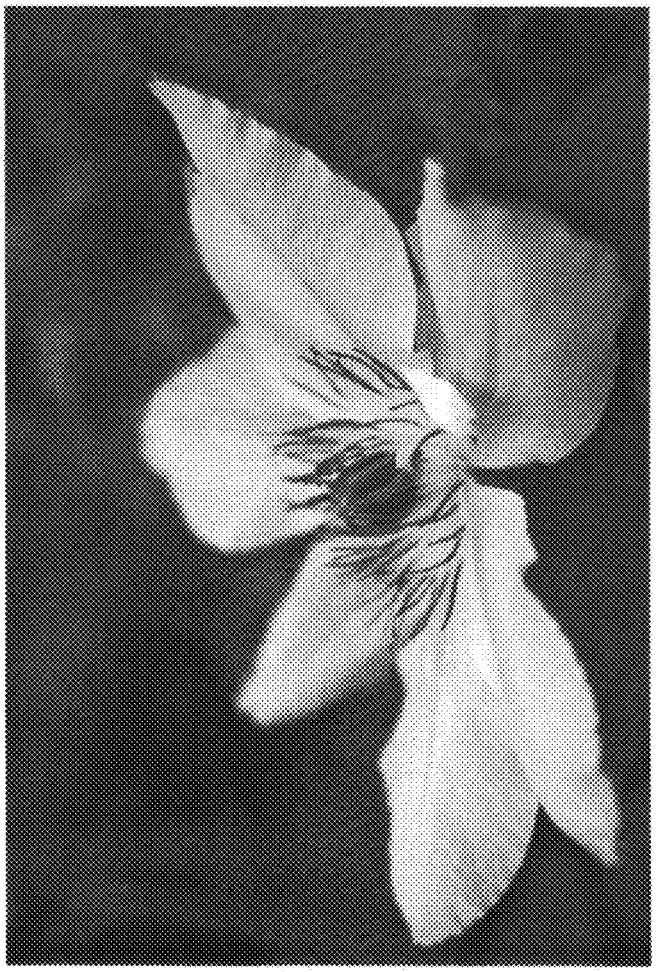

The accompanying photograph in FIG. 1 illustrates in full color a typical plant of 'YAKU050' grown outdoors in British Columbia, Canada. This plant is approximately 8 months old, grown in the ground. FIG. 2 illustrates in full color a typical flower of 'YAKU050'.

The photographs was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'YAKU050' plants grown outdoors in Waitara, New Zealand. Measurements were taken in Summer. The growing temperature ranged from approximately 2° C. to 25° C. at night to 8° C. to 30° C. during the day. No artificial light, photoperiod treatments or chemical treatments were given to the plants. Plants were pinched twice. Measurements and numerical values represent averages of typical flowering types.

Botanical classification: *Clematis* hybrid 'YAKU050'.
Age of the plant described: Approximately 8 months.
Growing conditions of the plant described: Growing in the ground.

PROPAGATION

Typical method: Vegetative cuttings.
Time to initiate rooting: Approximately 20 days at 21° C. or higher.
Time to produce a rooted plantlet: Approximately 40 days at 20° C. to 25° C.
Root description: Fine, fibrous.

PLANT

Growth habit: Climbing vine.
Height: Approximately 300 cm.
Plant spread: Approximately 150 cm.
Growth rate: Rapid. During active growing season in Spring, approximately 150 cm per month.
Branching characteristics: One main stem.
Length of main stem: Approximately 300 cm.
Diameter of main stem: Approximately 0.2 to 0.5 cm.
Main stem color: Near RHSGrey-Brown 199A when mature. Young stem near Yellow-Green N144C.
Main stem texture: Glabrous.
Internode length: Approximately 15 cm.
Strength: Strong, flexible, semi-woody.

FOLIAGE

Leaf:
*Arrangement*.—Opposite, ternate.
*Overall leaf length*.—Approximately 12 to 15 cm.
*Overall leaf diameter*.—Approximately 10 to 12 cm.
*Leaflets*.—Average Length: approximately 6 to 10 cm. Average Width: approximately 4.0 to 7.5 cm. Shape of blade: Oblong to cordate. Apex: Cuspidate. Base: Cordate.
*Attachment*.—Stalked.
*Margin*.—Entire.
*Texture of both surfaces*.—Slightly bullate.
*Color*.—Young foliage upper side: Near RHS Green 137A. Young foliage under side: Near RHS Green 137C. Mature foliage upper side: Near RHS Green 137A. Mature foliage under side: Near RHS Green 137C.
*Venation*.—Type: Pinnate. Venation color upper side: Near RHS Yellow-Green 145C. Venation color under side: Near RHS Yellow-Green 145B.
Petiole:
*Length*.—Approximately 2.0 to 5.0 cm.
*Diameter*.—Approximately 0.2 cm.
*Texture*.—Smooth.
*Color*.—Near RHS Greyed-Green 199A on upperside, Green 137B on lower surface.

FLOWER

Bloom period:
*Natural season*.—Continuously May through September.
Inflorescence type and habit: Single occurring, axillary; single flowers facing outward. Typically flowers on both new growth and previous year's growth.
Rate of flower opening: Approximately 7 days from bud to fully opened flower.
Flower longevity on plant: Approximately 8 to 12 days, after fully opened. Self-cleaning.
Inflorescence size:
*Diameter*.—Approximately 12 to 15 cm.
*Depth*.—Approximately 2.8 cm.
Corolla:
*Tepal arrangement*.—Single whorl, slightly overlapping.
*Quantity*.—Approximately 6 to 8 per flower.
*Shape*.—Obovate.
*Size*.—Length: Approximately 6 to 10 cm. Width: Approximately 3 to 4 cm.
*Margin*.—Slightly ruffled.
*Apex*.—Acute.
*Base*.—Rounded.
*Texture*.—Smooth.
Color:
*Tepals*.—When opening: Upper surface: Near RHS Purple 75D with bar near Red-Purple 72C. Lower surface: Near RHS Purple 75D. Fully opened: Upper surface: Near RHS Red-Purple 75D center bar near Red-Purple 72B, edges lighter near Purple 75A. Lower surface: Near RHS Red-Purple 70D with center bar near Yellow-Green 144C. Edges flushed near 71D.
*Ageing*.—Upper Surface: Near RHS Red-Purple 75D, bar near 70C. Lower Surface: Near RHS Red-Purple 75D.
Bud:
*Shape*.—Conical.
*Length*.—Approximately 2.5 cm.
*Diameter*.—Approximately 1.5 cm.
*Color*.—Near RHS White N155C, flushed Red-Purple 70D at apex.
Pedicels:
*Length*.—Approximately 10 to 25 cm.
*Width*.—Approximately 0.4 to 0.6 cm.
*Angle*.—Average 45° to 80°.
*Strength*.—Flexible.
*Color*.—Near RHS Green 137A.
Fragrance: None.

REPRODUCTIVE ORGANS

Stamens:
*Number*.—Approximately 70 to 85 per flower.
*Anther length*.—Approximately 0.5 cm.
*Anther color*.—Near RHS Greyed-Red 181D.
*Anther shape*.—Oblong.
*Filament length*.—Approximately 1.5.
*Filament color*.—Near RHS White N155D.
*Pollen quantity*.—Moderate.
*Pollen color*.—Greyed-Yellow 162D.
Pistil:
*Length*.—Approximately 2 cm.
*Style length*.—Approximately 0.6 cm.
*Stigma*.—Shape: Fine irregular hairs. Color: Near RHS Yellow-Green 154C, but lighter.

OTHER CHARACTERISTICS

Seeds: Moderate seed production, feathery seeds colored near Grey-Brown 199B.
Disease/pest resistance: Neither resistance nor susceptibility to normal diseases and pests of *Clematis* has been observed.
Temperature tolerance: Tolerates temperatures from approximately −20° C. to 45° C.

What is claimed is:

1. A new and distinct cultivar of *Clematis* hybrid plant named 'YAKU050' as herein illustrated and described.

* * * * *